(12) United States Patent
Franer

(10) Patent No.: US 7,163,525 B2
(45) Date of Patent: Jan. 16, 2007

(54) DUCKBILL SEAL PROTECTOR

(75) Inventor: Paul T. Franer, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 65 days.

(21) Appl. No.: 11/014,245

(22) Filed: Dec. 17, 2004

(65) Prior Publication Data

US 2006/0135978 A1   Jun. 22, 2006

(51) Int. Cl.
*A61M 5/178* (2006.01)
(52) U.S. Cl. .................. 604/167.03; 606/185; 606/167
(58) Field of Classification Search ............... 606/185, 606/167; 604/256, 167.01, 167.08, 167.06, 604/167.03, 34, 264, 104; 251/149.1
See application file for complete search history.

(56) References Cited

U.S. PATENT DOCUMENTS

| | | | |
|---|---|---|---|
| 3,504,699 A | 4/1970 | Grise | |
| 3,773,233 A | 11/1973 | Souza | |
| 4,436,519 A | 3/1984 | O'Neill | |
| 4,601,710 A | 7/1986 | Moll | |
| 4,610,665 A | 9/1986 | Matsumoto et al. | |
| 4,654,030 A | 3/1987 | Moll | |
| 4,902,280 A | 2/1990 | Lander | |
| 4,931,042 A | 6/1990 | Holmes et al. | |
| 4,932,633 A | 6/1990 | Johnson et al. | |
| 5,030,206 A | 7/1991 | Lander | |
| 5,053,013 A | 10/1991 | Ensminger et al. | |
| 5,104,383 A | 4/1992 | Shichman | |
| 5,203,773 A | 4/1993 | Green | |
| 5,209,737 A | 5/1993 | Ritchart et al. | |
| 5,211,634 A | 5/1993 | Vaillancourt | |
| 5,246,425 A | 9/1993 | Hunsberger et al. | |
| 5,300,033 A | 4/1994 | Miller | |
| 5,308,336 A | 5/1994 | Hart et al. | |
| 5,324,270 A | 6/1994 | Kayan et al. | |
| 5,330,437 A * | 7/1994 | Durman ................. 604/167.04 |
| 5,342,315 A | 8/1994 | Rowe et al. | |
| 5,366,445 A | 11/1994 | Haber et al. | |
| 5,385,552 A | 1/1995 | Haber et al. | |
| 5,385,553 A | 1/1995 | Hart et al. | |
| 5,441,041 A | 8/1995 | Sauer et al. | |
| 5,456,284 A | 10/1995 | Ryan et al. | |
| 5,467,762 A | 11/1995 | Sauer et al. | |
| 5,492,304 A * | 2/1996 | Smith et al. ............. 251/149.1 |
| 5,534,009 A | 7/1996 | Lander | |
| 5,542,931 A | 8/1996 | Gravener et al. | |
| 5,569,160 A | 10/1996 | Sauer et al. | |
| 5,578,016 A | 11/1996 | Zinger | |
| 5,584,850 A | 12/1996 | Hart et al. | |
| 5,603,702 A | 2/1997 | Smith et al. | |
| 5,628,732 A | 5/1997 | Antoon, Jr. et al. | |

(Continued)

FOREIGN PATENT DOCUMENTS

EP   0339945   11/1989

(Continued)

*Primary Examiner*—Nicholas D. Lucchesi
*Assistant Examiner*—Christopher D. Koharski

(57) ABSTRACT

A seal for use in conjunction with a trocar assembly includes a seal body adapted for selectively opening and closing the seal, and a protector adjacent the seal body for protecting the seal body from instruments passing through the seal body. The protector includes at least one flap mounted for pivotal movement, the flap including an inner edge located generally toward a center of the seal and an outer edge mounted to a support member which maintains the flap in a position above the seal body. The flap is shaped and dimensioned such that the majority of the seal body is covered by the outline of the flap.

18 Claims, 3 Drawing Sheets

U.S. PATENT DOCUMENTS

| | | |
|---|---|---|
| 5,643,301 A | 7/1997 | Mollenauer |
| 5,807,338 A | 9/1998 | Smith et al. |
| 5,865,812 A | 2/1999 | Correia |
| 5,895,377 A * | 4/1999 | Smith et al. ................ 604/256 |
| 6,024,729 A | 2/2000 | Dehdashtian et al. |
| 6,083,203 A * | 7/2000 | Yoon .................... 604/167.01 |
| 6,086,603 A | 7/2000 | Termin et al. |
| 6,277,100 B1 | 8/2001 | Raulerson et al. |
| 6,302,852 B1 | 10/2001 | Fleming, III et al. |
| 6,352,520 B1 | 3/2002 | Miyazaki |
| 6,569,120 B1 | 5/2003 | Green et al. |
| 6,613,063 B1 | 9/2003 | Hunsberger |
| 6,685,630 B1 | 2/2004 | Sauer et al. |
| 6,702,787 B1 | 3/2004 | Racenet et al. |
| 2002/0007153 A1 | 1/2002 | Wells et al. |
| 2002/0010425 A1 | 1/2002 | Guo et al. |
| 2002/0128602 A1 | 9/2002 | Adams et al. |
| 2004/0049173 A1 | 3/2004 | White et al. |
| 2004/0064100 A1 | 4/2004 | Smith |
| 2004/0147949 A1 | 7/2004 | Stellon et al. |

FOREIGN PATENT DOCUMENTS

| | | |
|---|---|---|
| EP | 0567142 | 10/1993 |
| EP | 0568383 | 11/1993 |
| EP | 0696459 | 2/1996 |
| WO | WO 94/03232 | 2/1994 |
| WO | WO 00/35529 | 6/2000 |
| WO | WO 2004/033004 | 4/2004 |

* cited by examiner

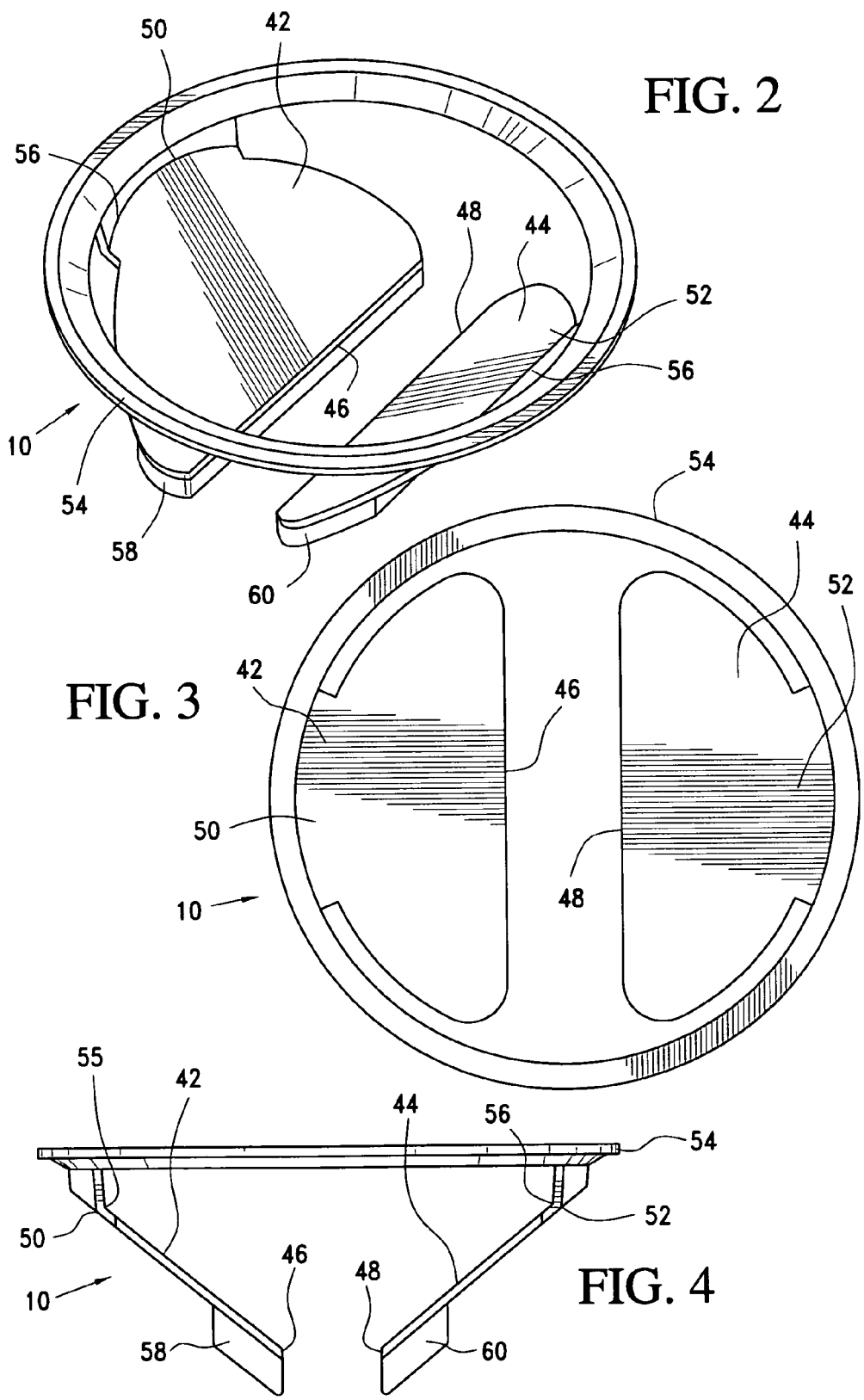

DUCKBILL SEAL PROTECTOR

BACKGROUND OF THE INVENTION

1. Field of the Invention

The invention relates to trocar assemblies. More particularly, the invention relates to a trocar sealing assembly including a protector minimizing detrimental contact between inserted instruments and the seal body.

2. Description of the Prior Art

A trocar assembly is a surgical instrument that is used to gain access to a body cavity. A trocar assembly generally comprises two major components, a trocar sleeve, composed of a trocar housing and a trocar cannula, and a trocar obturator. The trocar cannula, having the trocar obturator inserted therethrough, is directed through the skin to access a body cavity. Once the body cavity is accessed, laparoscopic or arthroscopic surgery and endoscopic procedures may be performed. In order to penetrate the skin, the distal end of the trocar cannula is placed against the skin that has been previously cut with a scalpel. The trocar obturator is then used to penetrate the skin and access the body cavity. By applying pressure against the proximal end of the trocar obturator, the sharp point of the trocar obturator is forced through the skin until it enters the body cavity. The trocar cannula is inserted through the perforation made by the obturator and the obturator is withdrawn, leaving the trocar cannula as an access way to the body cavity.

The proximal end portion of the trocar cannula is typically joined to a trocar housing that defines a chamber having an open distal end portion in communication with the interior lumen defined by the trocar cannula. A trocar obturator, or other elongated surgical instruments or tools, axially extend into and are withdrawn from the trocar cannula through the proximal end portion of the chamber defined by the trocar housing.

It is common for a sealing arrangement or sealing device to be used in association with the trocar cannula and trocar housing to prevent the escape of fluid or gas during endoscopic procedures. During an endoscopic surgical procedure, the internal gas pressure must be maintained in order to successfully complete the procedure. In order to maintain the internal gas pressure while instruments are passed into and out of the trocar sleeves positioned in the abdominal cavity, sealing devices are required for both the trocar obturator and instruments passing through he trocar cannula.

Seals must also offer good tear resistance, resistance to snagging and low friction with respect to the insertion or removal of surgical instruments. Angular insertion of instruments relative to the central axis of the trocar cannula and instrument tip sharpness are driving factors in trocar seal failures. These two factors can cause "tenting" of the seal material. Once tenting occurs, continued distal motion of the penetrating instrument will result in seal tearing.

As such, a need exists for a protector capable of protecting the seal as an obturator or instrument is passed through the trocar cannula. In particular, a need exist for a protector which may be used in conjunction with duckbill seals commonly utilized in trocar assemblies. The present invention provides such a protector.

SUMMARY OF THE INVENTION

It is, therefore, an object of the present invention to provide a seal for use in conjunction with a trocar assembly. The seal includes a seal body adapted for selectively opening and closing the seal, and a protector adjacent the seal body for protecting the seal body from instruments passing through the seal body. The protector includes at least one flap mounted for pivotal movement, the flap including an inner edge located generally toward a center of the seal and an outer edge mounted to a support member which maintains the flap in a position above the seal body. The flap is shaped and dimensioned such that the majority of the seal body is covered by the outline of the flap.

It is also an object of the present invention to provide a trocar assembly including a trocar cannula having a proximal end and distal end. A trocar housing is coupled to the proximal end of the trocar cannula for receiving and guiding an obturator through the trocar cannula. The trocar housing includes an open proximal end portion defining an opening provided with a seal assembly, the seal assembly including a protector for protecting a seal body of the seal assembly from instruments passing through the seal body. The protector includes at least one flap mounted for pivotal movement, the flap including an inner edge located generally toward the center of the seal and an outer edge mounted to a support member which maintains the flap in a position above the seal body. The flap is shaped and dimensioned such that the majority of the seal body is covered by an outline of the flap.

It is another object of the present invention to provide trocar assembly including a trocar cannula having a proximal end and distal end. A trocar housing is coupled to the proximal end of the trocar cannula for receiving and guiding an obturator through the trocar cannula. The trocar housing includes an open proximal end portion defining an opening provided with a proximal seal assembly and a distal seal assembly. The distal seal assembly includes a protector for protecting a seal body of the distal seal assembly from instruments passing through the seal body. The protector includes at least one flap mounted for pivotal movement. The flap includes an inner edge located generally toward the center of the seal and an outer edge mounted to a support member which maintains the flap in a position above the seal body, wherein the flap is shaped and dimensioned such that the majority of the seal body is covered by an outline of the flap.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a top perspective view of the protector in accordance with the present invention.

FIG. 3 is top view of the protector shown in FIG. 2.

FIG. 4 is a side view of the protector shown in FIG. 2.

DESCRIPTION OF THE PREFERRED EMBODIMENT

Figure 1:
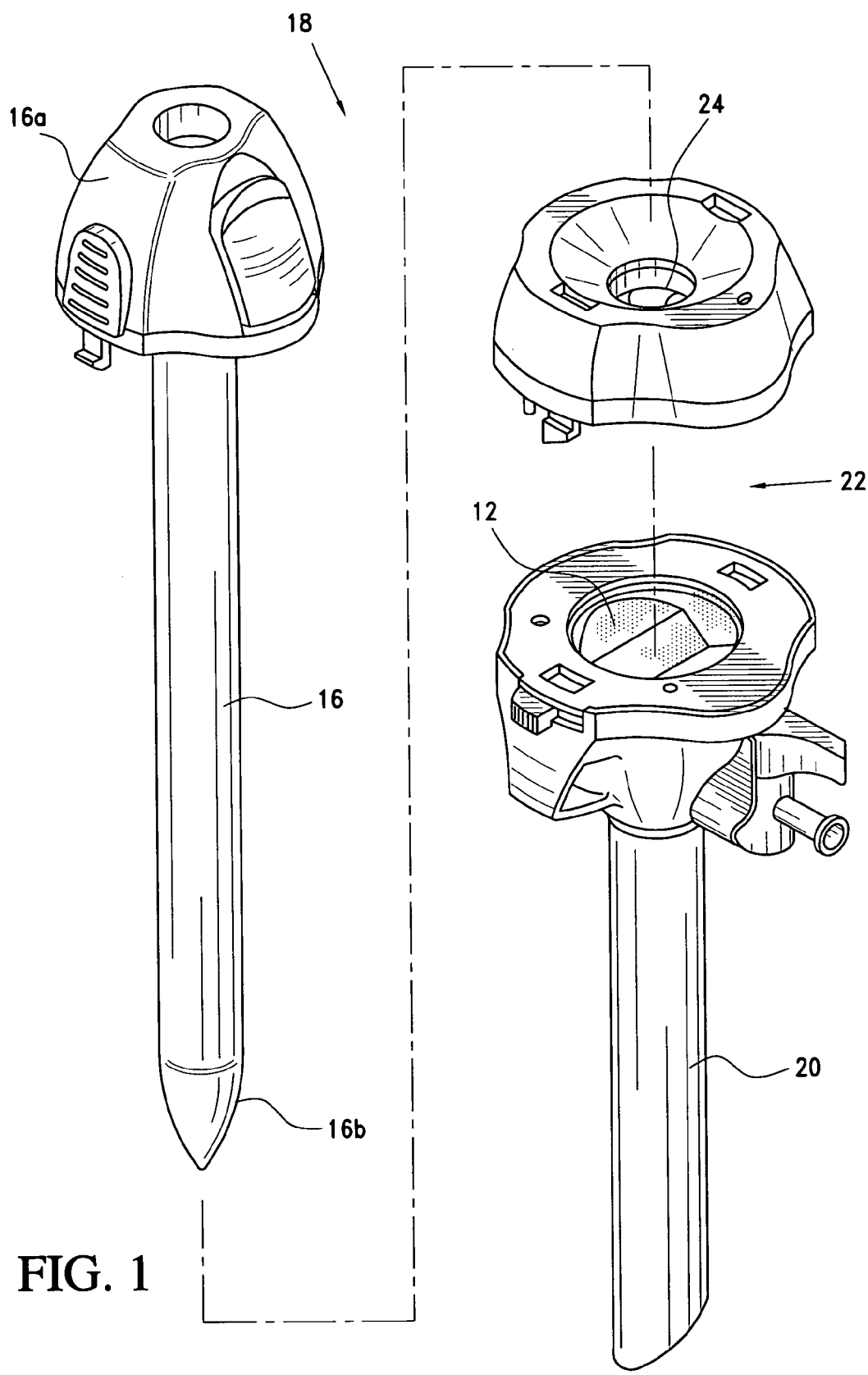
FIG. 1 is an exploded view of a trocar assembly in accordance with the present invention.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 to 6, a protector 10 for a duckbill seal assembly 12 in accordance with the present invention is disclosed. The protector 10 provides for improved resistance to tearing by protecting the seal body 14 from direct contact with trocar obturators 16 and instruments as they pass through the trocar housing 22 and trocar cannula 20.

The protector 10 is adapted for use with low cost surgical trocar assemblies 18 utilized for minimally invasive endoscopic surgical procedures, including but not limited to, laparoscopic and arthroscopic surgical procedures. Such surgical trocar assemblies are disposable and are intended to be used as a single patient use only device.

Apart from the duckbill seal assembly 12, including the protector 10, in accordance with the present invention, the general structure of the trocar assembly 18 does not form part of the present invention. For example, and by way of explaining the present duckbill seal assembly 10, the trocar assembly 18 may take a variety of forms known to those skilled in the art.

With that in mind, and by way of example, the trocar assembly 18 includes a trocar cannula 20, a trocar obturator 16, and a trocar housing (or handle) 22. The trocar cannula 20 defines an interior lumen having an open distal end portion and an open proximal end portion. The proximal end portion extends into and is mounted in the distal end portion of trocar housing 22. The trocar housing 22 has an open proximal end portion that defines an opening with proximal seal assembly 24 positioned therein. A duckbill seal assembly 12 is positioned beneath the proximal seal assembly 24 for selectively sealing the opening of the trocar housing 22.

The trocar obturator 16 is slidably and removably extendable within the trocar cannula 20. It is inserted into the trocar housing 22 and the trocar cannula 20, and extends through the proximal seal assembly 24 and the duckbill seal assembly 12. An obturator handle 16a is provided at the proximal end of the trocar obturator 16 and a sharpened point or blade 16b is formed at the distal end thereof. As is well known in the art, the proximal seal assembly 24 cooperates with the trocar obturator 16, or other surgical instrument extending through the trocar cannula 20, to sealingly engage the outer surface thereof and thereby preclude the passage of fluids through the trocar housing 22.

As mentioned above, the duckbill seal assembly 12 is supported beneath the proximal seal assembly 24. The duckbill seal assembly 12 in accordance with a preferred embodiment of the present invention includes first and second seal bodies 28, 30 extending from a circumferential flange member 32 shaped and dimensioned for mounting within the trocar housing 22. Each of the first and second seal bodies 28, 30 includes an upper surface and a lower surface. The upper surface and the lower surface are generally mirror images as the first and second seal 28, 30 bodies maintain a substantially consistent thickness along their entire lengths, with the exception of ribs commonly employed on the upper surface of duckbill seal bodies.

As mentioned above the seal assembly 12 is provided with a protector 10 positioned adjacent the seal bodies 28, 30 for the purpose of protecting the seal bodies 28, 30 as trocar obturator 16 and instruments are passed through the trocar cannula 20. The protector 10 functions to protect the seal bodies 28, 30 of the duckbill seal assembly 12 from tearing as a result of contact or penetration via sharp surgical instruments inserted through the trocar housing 22. The present protector 10 provides for improved reliability of maintaining insufflation during laparoscopic surgical procedures.

The protector 10 in accordance with a preferred embodiment of the present invention is molded plastic, for example, pellethane. However, it is not intended that the protector 10 be limited merely to molded plastic, but the protector 10 may be made from any type of material that contains the required properties and characteristics for the function described herein.

With reference to FIGS. 2, 3, 4, 5 and 6, the protector 10 is shown in greater detail. The protector 10 is designed for protecting the seal bodies 28, 30 of duckbill seal assemblies 12 used in conjunction with trocar assemblies 18. The protector 10 hangs just above the upper surface 34, 36 of the seal bodies 28, 30 and is made of a tear resistant material.

The protector 10 includes two opposed protector flaps 42, 44. Each of the first and second flaps 42, 44 include an inner edge 46, 48 located generally toward the center of the trocar housing 22 and an outer edge 50, 52 located generally toward the wall of the trocar housing 22. The outer edges 50, 52 of the first and second flaps 42, 44 are respectively hinged to an outer support member, which is shown in accordance with a preferred embodiment as a ring 54, extending around and supporting the first and second flaps 42, 44.

Figure 5:
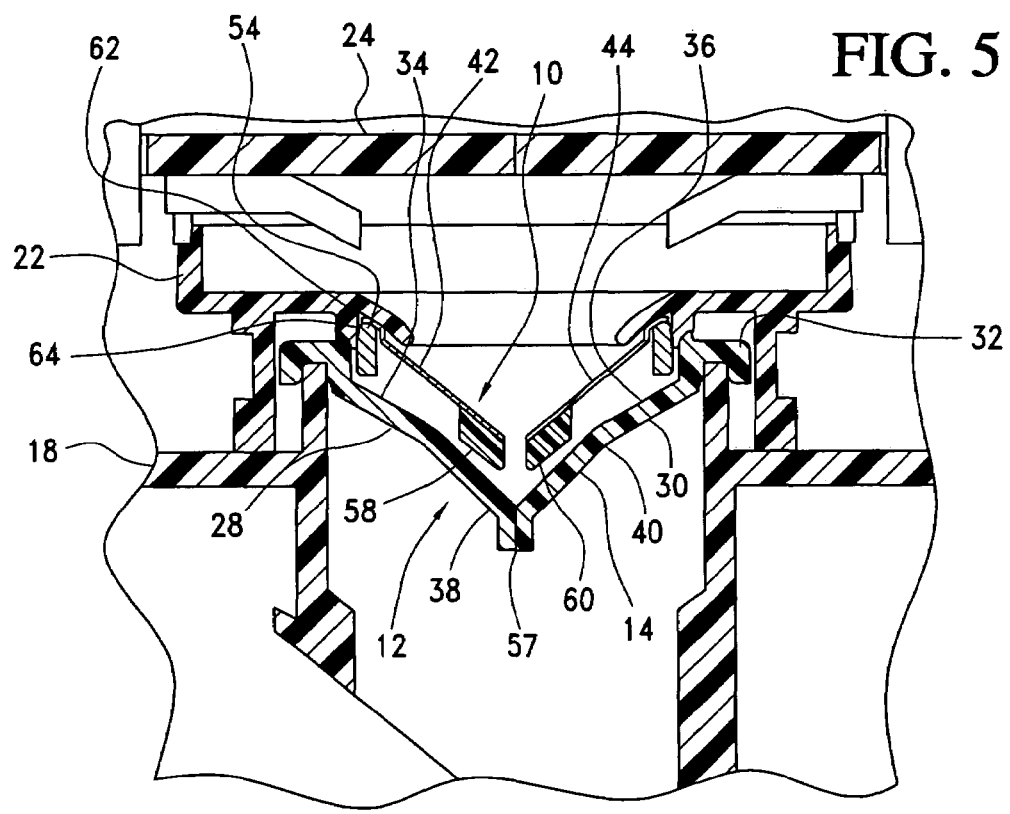
FIGS. 5 and 6 respectively show cross sectional view of the trocar housing with and without a trocar obturator extending therethrough.
Figure 6:
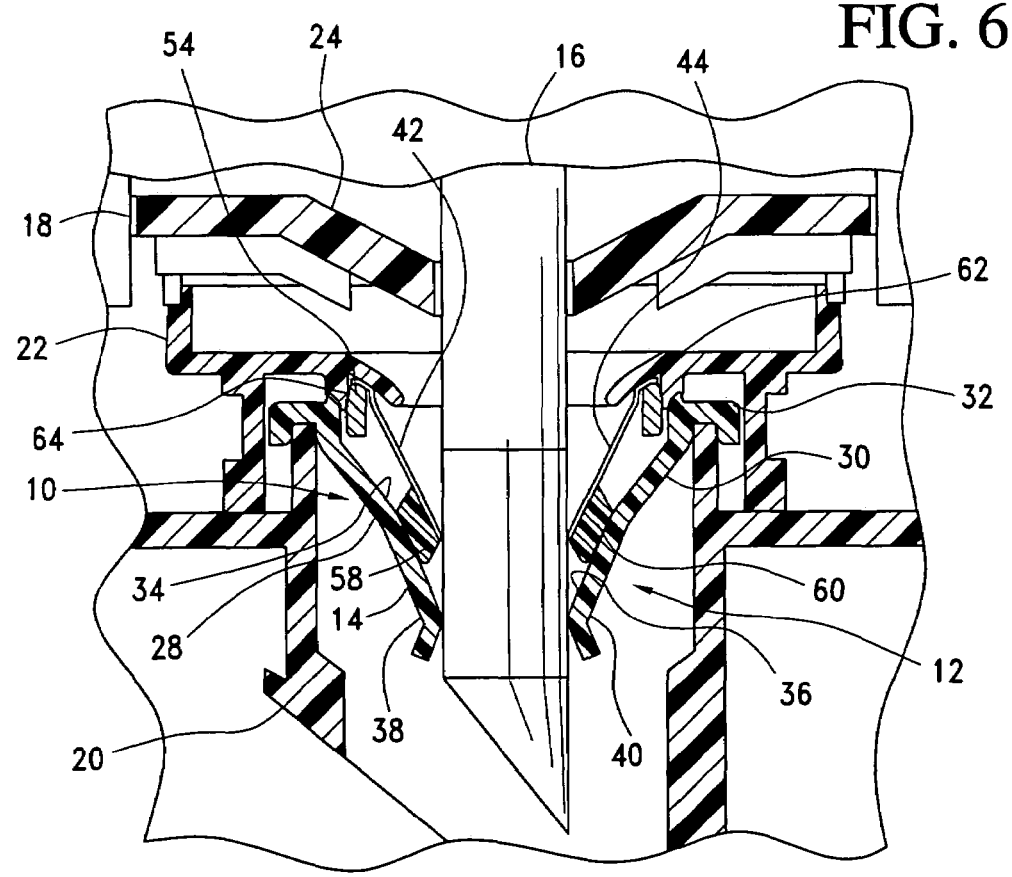

With reference to FIGS. 5 and 6, the outer support ring 54 is shaped and dimensioned for positioning within the trocar housing 22 in a manner which permits positioning of the first and second flaps 42, 44 above the seal bodies 28, 30 of the duckbill seal assembly 12. As such, those skilled in the art will readily appreciate that the outer support ring 54 and the first and second flaps 42, 44 may be varied for use with different trocar assembly structures without departing from spirit of the present invention. Although the protector in accordance with a preferred embodiment of the present invention is designed for use with duckbill seals having only two flaps, those skilled in the art will appreciate that the concepts underlying the present invention may be applied to configurations employing more than two flaps. In addition, the concepts underlying the present invention may be applied to a variety of duckbill seals, for example, those exhibiting a cruciform shape, without departing from the spirit of the present invention. The hinges 55, 56 connecting the first and second flaps 42, 44 to the outer support ring 54 allow them to deflect both downward and upward as required by the movement of instruments inserted through the trocar cannula 20 and trocar housing 22. For example, downward deflection would be required during instrument insertion and upward deflection would be required during instrument extraction.

The protector flaps 42, 44 are shaped and dimensioned such that the majority of the respective upper surfaces 34, 36 of the seal bodies 28, 30 are covered by the outline of the protector flaps 42, 44. During instrument insertion (for example, a trocar obturator 16), and as shown in FIG. 6, the protector flaps 42, 44 guard the seal bodies 28, 30 of the duckbill seal assembly 12 from tearing by camming the seal bodies 28, 30 out of the way to an extent that the instrument can pass through the slit 57 in the center of the duckbill seal assembly 12. This is accomplished by providing the first and second flaps 42, 44 with camming surfaces 58, 60 along their undersides. The camming surfaces 58, 60 are shaped and dimensioned to force the duckbill seal assembly 12 toward an open configuration as the instrument moves toward the first and second seal bodies 28, 30 and past the protector 10. The protector 10 does not open the seal bodies 28, 30 of the duckbill seal assembly 12 until the instrument contacts the protector 10, at which point the protector 10 transfers that force to the seal bodies 28, 30, thus opening the duckbill seal assembly 12 prior to direct contact with the instrument. As a result, direct contact with the instrument is reduced and the likelihood for tearing is similarly reduced.

In accordance with a preferred embodiment, the present protector 10 is attached to the underside of the outer-seal base 62 of the trocar housing 22. More specifically, the outer support ring 54 is seated within the recess 64 formed in the underside of the outer-seal base 62 of the trocar housing 22. The outer support ring 54 is rigidly connected thereto by press fitting the outer support ring 54 within the recess 64 such that the outer support ring 54 is trapped therein. While a preferred mechanism for mounting the present protector 10 with the trocar housing 22 is disclosed above, those skilled in the art will appreciate that various mechanism for mounting the protector 10 may be employed without departing from the spirit of the present invention.

It should be noted that the first and second flaps 42, 44 of the protector 10 do not need to cover the entire surface of the seal bodies 28, 30 of the duckbill seal assembly 12 all the way to the center of the seal assembly 12. Full coverage is not required because an instrument contacting an unprotected duckbill seal body 28, 30 near the center will simply pass through the duckbill seal assembly 12 without contacting the seal bodies 28, 30 in a manner that might cause damage thereto. However, the closer the instrument contact is to the perimeter of the duckbill seal assembly 12, the more likely the seal bodies 28, 30 are to "tent" and tear. Protection, therefore, is needed less toward the center of the duckbill seal assembly 12, and more at the perimeter. The first and second flaps 42, 44 of the protector 10 protect the seal bodies 28, 30 to an undefined point along the surface of the seal bodies 28, 30 where instrument contact is likely to cause tearing.

Although the concept shown has a single protector, the design could also be executed using multiple individual protectors. Although, the protector does not need to protect fully to the center where the seal bodies meet, it can if desired.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A seal for use in conjunction with a trocar assembly, comprising:
 a circumferential flange having a seal body extending therefrom, the seal body being adapted for selectively opening and closing to seal an opening of the trocar assembly when an instrument is not passed therethrough, wherein the seal body includes an upper surface;
 a protector adjacent the seal body for protecting the seal body from instruments passing through the seal body; the protector including:
  at least one flap positioned above the seal body and mounted for pivotal movement, the flap including an inner edge located generally toward a center of the seal and an outer edge mounted to a support member which maintains the flap in a position above the seal body, wherein the flap is shaped and dimensioned such that the majority of the upper surface of the seal body is covered by the outline of the flap so as to protect the upper surface of the seal body from an instrument passing therethrough;
 wherein the instrument contacts the protector during insertion of the instrument forcing an underside of the flap into contact with the seal body in a manner forcing the seal body to an open configuration, this results in a transfer of force from the instrument to the protector to the seal body to open the seal body prior to direct contact with the instrument to thereby reduce direct contact between the instrument and the seal body and minimize a likelihood for tearing, and wherein the instrument first contacts the protector and then the seal body during insertion.

2. The seal according to claim 1, wherein the seal is a duckbill seal.

3. The seal according to claim 1, wherein the protector includes first and second opposed flaps, each flap including an inner edge located generally toward the center of the seal and an outer edge mounted to the support member which maintains the flaps in relation above the seal body.

4. The seal according to claim 3, wherein the support member is a support ring shaped and dimensioned for positioning within a trocar assembly in a manner which permits positioning of the first and second flaps above the seal.

5. The seal according to claim 3, wherein the outer edges of the respective first and second flaps are respectively hinged to the support member in a manner which allows the first and second flaps to deflect both downward and upward as required by the movement of instruments passing through the trocar assembly.

6. The seal according to claim 1, wherein the flap includes an underside in facing relation with the seal body, the underside of the flap including a caniming surface which contacts the seal body during insertion of an instrument to force the seal body out of the way to an extent that an instrument can pass through a seal opening in the center of the seal body.

7. A trocar assembly, comprising:
 a trocar cannula including a proximal end and distal end; and
 a trocar housing coupled to the proximal end of the trocar cannula for receiving and guiding an obturator through the trocar cannula, the trocar housing includes an open proximal end portion defining an opening provided with a seal assembly, the seal assembly including a circumferential flange having a seal body extending therefrom, the seal body being adapted for selectively opening and closing to seal an opening of the trocar assembly when an instrument is not passed therethrough, wherein the seal body includes an upper surface, and a protector for protecting the seal body of the seal assembly from instruments passing through the seal body; the protector including at least one flap positioned above the seal body and mounted for pivotal movement, the flap including an inner edge located generally toward the center of the seal and an outer edge mounted to a support member which maintains the flap in a position above the seal body, wherein the flap is shaped and dimensioned such that the majority of the upper surface of the seal body is covered by an outline of the flap so as to protect the upper surface of the seal body from an instrument passing therethrough, wherein the instrument contacts the protector during insertion of the instrument forcing an underside of the flap into contact with the seal body in a manner forcing the seal body to an open configuration, this results in a transfer of force from the instrument to the protector to the seal body to open the seal body prior to direct contact with the instrument to thereby reduce direct contact between the instrument and the seal body and minimize a likelihood for tearing, and wherein the instrument first contacts the protector and then the seal body during insertion.

8. The trocar assembly according to claim 7, wherein the seal assembly is a duckbill seal assembly.

9. The trocar assembly according to claim 7, wherein the protector includes first and second opposed flaps, each flap including an inner edge located generally toward a center of the seal body and an outer edge mounted to the support member which maintains the flaps in relation above the seal body.

10. The trocar assembly according to claim 9, wherein the support member is a support ring shaped and dimensioned for positioning within a trocar assembly in a manner which permits positioning of the first and second flaps above the seal body.

11. The trocar assembly according to claim 9, wherein the outer edges of the respective first and second flaps are respectively hinged to the support member in a manner which allows the first and second flaps to deflect both downward and upward as required by the movement of instruments passing through the trocar assembly.

12. The trocar assembly according to claim 7, wherein the flap includes an underside in facing relation with the seal body, the underside of the flap including a camming surface which contact the seal body during insertion of an instrument to force the seal body out of the way to an extent that an instrument can pass through the seal opening in the center of the seal body.

13. A trocar assembly, comprising:
a trocar cannula including a proximal end and distal end; and
a trocar housing coupled to the proximal end of the trocar cannula for receiving and guiding an obturator through the trocar cannula, the trocar housing includes an open proximal end portion defining an opening provided with a proximal seal assembly and a distal seal assembly, the distal seal assembly including a circumferential flange having a seal body extending therefrom, the seal body being adapted for selectively opening and closing to seal the opening of the trocar assembly when an instrument is not passed therethrough, wherein the seal body includes an upper surface, and a protector for protecting a seal body of the distal seal assembly from instruments passing through the seal body; the protector including at least one flap positioned above the seal body and mounted for pivotal movement, the flap including an inner edge located generally toward the center of the seal and an outer edge mounted to a support member which maintains the flap in a position above the seal body, wherein the flap is shaped and dimensioned such that the majority of the upper surface of the seal body is covered by an outline of the flap so as to protect the upper surface of the seal body from an instrument passing therethrough, wherein the instrument contacts the protector during insertion of the instrument forcing an underside of the flap into contact with the seal body in a manner forcing the seal body to an open configuration, this results in a transfer of force from the instrument to the protector to the seal body to open the seal body prior to direct contact with the instrument to thereby reduce direct contact between the instrument and the seal body and minimize a likelihood for tearing, and wherein the instrument first contacts the protector and then the seal body during insertion.

14. The trocar assembly according to claim 13, wherein the distal seal assembly is a duckbill seal assembly.

15. The trocar assembly according to claim 13, wherein the protector includes first and second opposed flaps, each flap including an inner edge located generally toward a center of the seal body and an outer edge mounted to the support member which maintains the flaps in relation above the seal body.

16. The trocar assembly according to claim 15, wherein the support member is a support ring shaped and dimensioned for positioning within a trocar assembly in a manner which permits positioning of the first and second flaps above the seal body.

17. The trocar assembly according to claim 15, wherein the outer edges of the respective first and second flaps are respectively hinged to the support member in a manner which allows the first and second flaps to deflect both downward and upward as required by the movement of instruments passing through the trocar assembly.

18. The trocar assembly according to claim 13, wherein the flap includes an underside in facing relation with the seal body, the underside of the flap including a camming surface which contact the seal body during insertion of an instrument to force the seal body out of the way to an extent that an instrument can pass through the seal opening in the center of the seal body.

* * * * *